(12) United States Patent
Thompson

(10) Patent No.: US 7,662,373 B2
(45) Date of Patent: Feb. 16, 2010

(54) METHOD AND COMPOSITION OF A MEDICAMENT TO DECREASE THE ADVERSE EVENTS OF OLISTAT, AN ORAL LIPASE INHIBITOR

(76) Inventor: Ronald J. Thompson, 110 Stanbery Ridge, Fort Thomas, KY (US) 41075

( * ) Notice: Subject to any disclaimer, the term of this patent is extended or adjusted under 35 U.S.C. 154(b) by 0 days.

(21) Appl. No.: 11/654,361

(22) Filed: Jan. 16, 2007

(65) Prior Publication Data

US 2008/0070977 A1  Mar. 20, 2008

Related U.S. Application Data

(62) Division of application No. 11/522,627, filed on Sep. 18, 2006, now abandoned.

(51) Int. Cl.
*A61K 33/44* (2006.01)
*A61K 31/695* (2006.01)
*A61K 31/335* (2006.01)

(52) U.S. Cl. .................... 424/125; 514/63; 514/449

(58) Field of Classification Search .............. None
See application file for complete search history.

(56) References Cited

U.S. PATENT DOCUMENTS

| 5,980,944 A | * | 11/1999 | Stevens et al. | 424/470 |
| 2004/0105838 A1 | * | 6/2004 | Barbier et al. | 424/78.12 |
| 2006/0229261 A1 | * | 10/2006 | Devane | 514/25 |
| 2007/0053899 A1 | * | 3/2007 | McFarland | 424/125 |

FOREIGN PATENT DOCUMENTS

| JP | 11029485 A | * | 2/1999 |
| JP | 2003026585 A | * | 1/2003 |

OTHER PUBLICATIONS

Liu et al, Enteric-coated peppermint-oil capsules in the treatment of irritable bowel syndrome: a prospective, randomized trial, Journal of gastroenterology, (Dec. 1997) vol. 32, No. 6, pp. 765-768.*

* cited by examiner

*Primary Examiner*—Terry A. McKelvey
*Assistant Examiner*—Qiuwen Mi
(74) *Attorney, Agent, or Firm*—Don Halgren

(57) ABSTRACT

A medicament to decrease the adverse events of Olistat, an oral lipase inhibitor, arranged in combination with Olistat, comprising: an emulsifier, a bowel relaxant and one or more chelating agents to absorb and mechanically agitate non-digested fats.

1 Claim, 1 Drawing Sheet

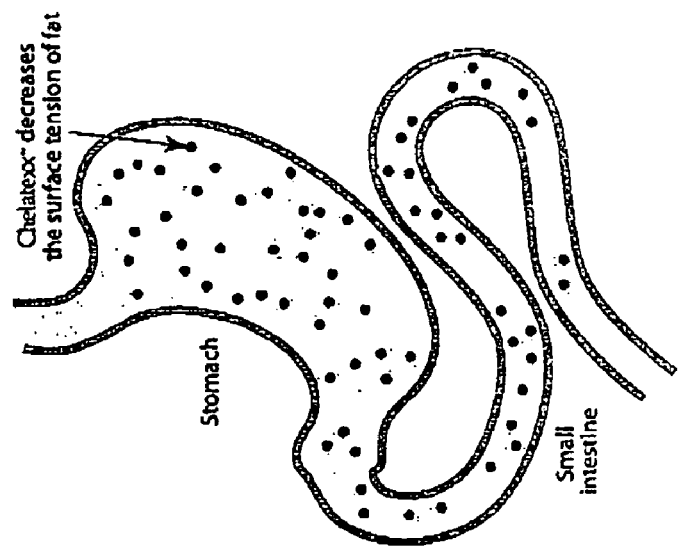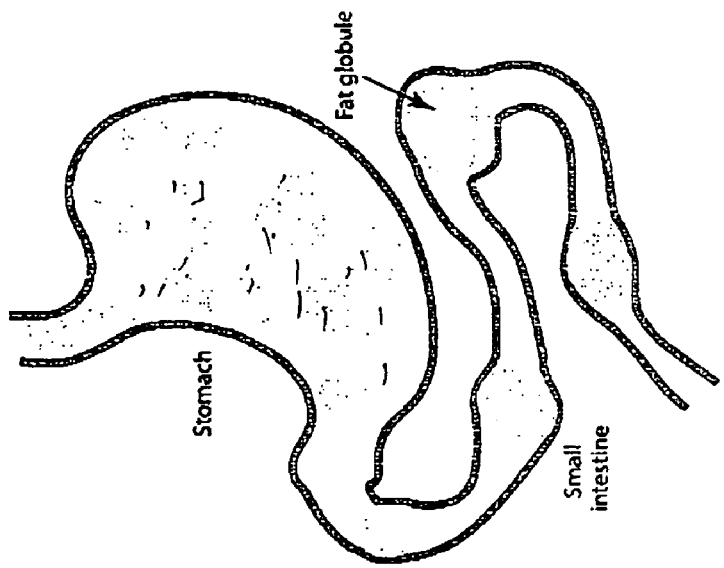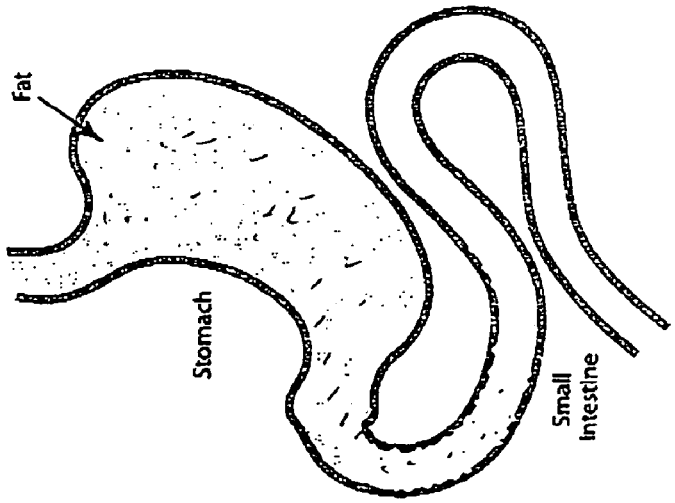

METHOD AND COMPOSITION OF A MEDICAMENT TO DECREASE THE ADVERSE EVENTS OF OLISTAT, AN ORAL LIPASE INHIBITOR

FIELD OF THE INVENTION

This application is a divisional of U.S. application Ser. No. 11/522,627, filed on 18 Sep. 2006 (abandoned on 30 Jul. 2007), and is incorporated herein by reference in its entirety.

This invention relates to drugs and medicaments for use in weight loss programs and more particularly for improvements in the use of a pharmaceutical known as Orlistat.

1. Background of the Invention and Prior Art

Orlistat is the generic name for Xenical® (Roche), a prescription lipase inhibitor, FDA approved for weight loss and obesity management. Lipase is the pancreatic enzyme that breaks down ingested fats into small chain fatty acids in the lower lumen of the stomach, and the small intestine. By inhibiting the actions of the lipase enzyme, ingested fats cannot be absorbed, and weight loss naturally occurs. The problem with Olistat treatment is, the most undesirable side effects are caused by the passage of the undigested fats through the gastrointestinal tract! The Physicians Desk Reference lists the adverse events (side effects) of Olistat clinical trials on over 2800 patients for one or two years as:

Upper gastrointestinal adverse events

| | |
|---|---|
| Abdominal pain/discomfort | 25.5% |
| Nausea | 8.1% |

Lower gastrointestinal adverse events

| | |
|---|---|
| Oily spotting | 26.6% |
| Flatus - with discharge | 23.9% |
| Fecal urgency | 22.1% |
| Fatty/oily stool | 26.0% |
| Oily evacuation | 11.9% |
| Increased defecation | 10.8% |
| Fecal incontinence | 7.7% |

Orlistat, as a lipase inhibitor, creates a mal-absorption state, where ingested fats are not absorbed by the intestine, and therefore must be eliminated through the lower intestine and rectum. All of the adverse events are directly caused by the elimination of large sized fat globules.

2. Prior Art

The chemical name for Orlistat is tetrahydrolipstatin. U.S. Pat. No. 4,598,089 issued Jul. 1, 1986, incorporated herein by reference in its entirety, defines tetrahydrolipstatin, and teaches its unique lipase inhibitor actions. These actions are further defined in U.S. Pat. Nos. 5,245,056 and 5,399,720, (both incorporated herein by reference), to treat obesity and various medical conditions associated with obesity, specifically diabetes and hypertension. U.S. Pat. No. 6,696,467, (incorporated herein by reference) further teaches and defines the specific benefits of the lipase inhibitor tetrahydrolipstatin for the treatment of obesity by weight reduction and appetite suppression. U.S. Pat. No. 6,004,996 (incorporated herein by reference), describes the production of tetahydrolipstatin into microspheres for optimal therapeutic delivery into the lumen of the stomach. These microspheres have a very efficient action as a lipase inhibitor, because of the large surface area to bind to the lipase enzyme.

DESCRIPTION OF THE DRAWINGS

The objects and advantages of the present invention will become more apparent when viewed in conjunction with the following drawings, in which:

FIG. 1 represents an outline of a stomach and intestine showing a Lipase enzyme released and breaking down fat;

FIG. 2 represents the outline of FIG. 1 showing Olistat blocking the Lipase enzyme to prevent the absorption of fat; and FIG. 3, represents the outline of FIG. 2, with a chelate admixed therewith, which decreases the surface tension of the fat to prevent the formation of large fat globules.

DESCRIPTION OF THE PRESENT INVENTION

The present invention is an arrangement to decrease the adverse events caused by the pharmaceutical agent Orlistat in weight loss therapy. The present invention is a combination of several chemicals, that function synergistically with one another to provide decreased signs and symptoms of the Orlistat adverse events. These agents are:

1. An Emulsifier
2. A bowel relaxant
3. One or more chelating agents as Mechanical Agitators 1. Emulsifiers All fats will aggregate together to form large fat globules relative to La Place's law of Surface Tension. An emulsifier added to the undigested fats in the lumen of the stomach and the small intestine will insure that the fats remain in a very small state as an emulsion. The detergent-like actions on the fats will directly decrease the signs and symptoms of Orlistat by preventing the formation of large fat globules, the pathogenesis of many of the adverse events. The emulsifier will also insure that the fats are in a small enough state to be adequately absorbed by the chelating agents. Simethicone is the best emulsifying agent and represents the class of emulsifiers, but other emulsifying agents could be utilized such as for example:

Stearoxy dimethicone,
Dimethicone,
Methicone,
Amino bispropyl dimethicine,
Amino propyl dimethicine,
Amodimethicone,
Amodimethicine hydroxysterate,
Beheroxy dimethricine,
C24-28 alkyl methicine,
C30-45 alkyl methicine,
C30-45 alkyl dimethicine,
Certearyl methicine and
Cetyl Dimethicine.

2. Bowel Relaxant

Menthol or a related cooling compound has a direct effect on both small bowel and large bowel musculature to relax the smooth muscle tone and reduces bowel irritability. The synergistic effect of decreasing general bowel irritability with a menthol compound, and decreasing the irritant effects of large undigested fat globules with both emulsification and chelation provides multiple mechanisms to decrease Orlistat induced adverse events. A list of potential menthol compounds and related cooling compounds is Menthol or any cooling agent listed below, having a concentration of less than 0.5% and greater than 0.01%;
   a) Wherein said cooling agent includes Menthol,
   b) wherein said cooling agent includes peppermint oil,
   c) wherein said cooling agent includes cornmint oil, d) wherein said cooling agent includes Eucalyptus oil,
e) wherein said cooling agent includes Citronella oil,
f) wherein said cooling agent includes Camphor oil,
g) wherein said cooling agent includes Cinnamon oil,
h) Wherein said cooling agent essentially comprises Menthol,
i) wherein said cooling agent essentially comprises peppermint oil,
j) wherein said cooling agent essentially comprises cornmint oil,
k) wherein said cooling agent essentially comprises Eucalyptus oil,
l) wherein said cooling agent essentially comprises Citronella oil,
m) wherein said cooling agent essentially comprises Camphor oil,
n) wherein said cooling agent essentially comprises Cinnamon oil,
o) wherein said cooling agent includes a menthol analog or derivative with cooling properties selected from:
Menthol Analogs and Derivatives:
(+)-neo-Menthol,
Menthone,
(+)-iso-Menthone,
Menthyl acetate,
Menthyl isovalerate,
(−)-Menthyl lactate,
para-menth-1-en-3ol,
Piperitone,
(−)-Menthol ethylene glycol carbonate,
(−)-Menthol 1-and 2-propylene glycol carbonate,
(−)-Menthone 1,2-glycerol ketal,
(+)-Menthone 1,2-glycerol ketal, and
mono-Menthyl succinate.

3. Chelating Agents as Mechanical Activators

Once in a small enough physical state by the actions of the emulsifying agent, the chelating agent will absorb the undigested unabsorbed fat from the stomach and small intestine to decrease Orlistat related adverse events. The hallmark chelating agent in treatment of toxic poisoning is activated carbon (activated charcoal). Activated carbon is not absorbed, but remains in the gastrointestinal tract and eliminated with bowel movements. The activated carbon will chelate free fats in the gastrointestinal lumens. A second chelating agent is cellulose or methylcellulose a non-fermentable fiber that will, like activated carbon, chelate the small emulsified fats that result from orlistat therapy. Any chelating agent could be utilized, but activated carbon and methylcellulose are the most effective.

A second mode of action of the chelating agents, activated charcoal, is to physically and mechanically decrease the surface tension of undigested fats. This is a mechanism which have the inert granules and methylcellulose fibers, are kept in a churning motion in the small intestine by the inherent peristalsis of the circular smooth muscles of the small intestines. This churning motion mechanically disrupts the formation of large fat globules. The two mechanisms to decrease surface tension, chemical and mechanical, synergistically function to prevent the formation of large fat globules, the pathogenesis of the adverse events of Orilstat.

For the best mode of such agents and actuators, the product would contain (preferable ranges), for example:
Simethicine 125 mg/capsule 50-200 mg,
Peppermint 90 mg/ capsule 500-200 mg,
Activated Carbon 300 mg/capsule 100-500 mg,
Methyl cellulose 200 mg/capsule 100-400 mg, and be ingested three times per day with or just after each meal, with Orlistat.

The present invention is also represented through the FIGS. 1, 2 and 3. In FIG. 1, the Lipase enzyme is released and breaks down the fat in the stomach, allowing that fat to be absorbed in the bloodstream in a normal manner. In FIG. 2, Olistat, the chemical name for products such as Xenical® and Alli™ are shown blocking the Lipase enzyme which prevents the absorption of fat. This also allows the formation of large fat globules. FIG. 3 represents the blocking of the Lipase enzyme by Xenical or Alli, preventing the absorption of fat, with the present invention, having the trademarked name of Chelatexx™. The Chelatexx includes the components of an emulsifier, a bowel relaxant and a chilating agent/mechanical actuator.

I claim:

1. A method to decrease the adverse effects of Orlistat in a subject comprising orally administering to the subject Orlistat, simethicone, and activated carbon.

* * * * *